United States Patent
Stone et al.

(10) Patent No.: US 6,210,440 B1
(45) Date of Patent: Apr. 3, 2001

(54) ANTERIOR CRUCIATE LIGAMENT XENOGRAFTS

(76) Inventors: Kevin R. Stone, 1 Throckmorthon La., Mill Valley, CA (US) 94941; Uri Galili, 9 Woodstream Dr., Wayne, PA (US) 19087

(*) Notice: Subject to any disclaimer, the term of this patent is extended or adjusted under 35 U.S.C. 154(b) by 0 days.

(21) Appl. No.: 09/036,087

(22) Filed: Mar. 6, 1998

Related U.S. Application Data

(63) Continuation-in-part of application No. 08/529,199, filed on Sep. 15, 1995.

(51) Int. Cl.[7] .......................................................... A61F 2/08
(52) U.S. Cl. ..................................... 623/13.11; 623/13.17; 623/901
(58) Field of Search .................................... 623/13, 1, 11, 623/12, 14, 15, 16, 901, 13.11, 13.14, 13.17

(56) References Cited

U.S. PATENT DOCUMENTS

| | | |
|---|---|---|
| 4,034,418 | 7/1977 | Jackson et al. . |
| 4,344,193 | 8/1982 | Kenny . |
| 4,400,833 | 8/1983 | Kurland . |
| 4,502,161 | 3/1985 | Wall . |
| 4,597,266 | 7/1986 | Entrekin . |
| 4,609,627 | 9/1986 | Goldstein . |
| 4,627,853 | 12/1986 | Campbell et al. . |
| 4,642,120 | 2/1987 | Nevo et al. . |

(List continued on next page.)

FOREIGN PATENT DOCUMENTS

| | | |
|---|---|---|
| WO 84/03036 | 8/1984 | (WO) . |
| WO 95/26740 | 10/1995 | (WO) . |
| WO 95/28412 | 10/1995 | (WO) . |
| WO 95/33828 | 12/1995 | (WO) . |

OTHER PUBLICATIONS

Rodrigo et al., *Clinical Orthopedics and Related Research*, 134:342–349 (1978).
Sengupta et al., *The Journal of Bone and Joint Surgery*, 56B:167–177 (1974).
Webber et al., *Journal of Orthopedic Research*, 3:36–42 (1985).
Rubak et al., *Acta Orthop. Scand*, 53:181–186 (1982).

(List continued on next page.)

*Primary Examiner*—David J. Isabella
*Assistant Examiner*—Choon P. Koh
(74) *Attorney, Agent, or Firm*—McDermott, Will & Emery

(57) ABSTRACT

The invention provides a substantially non-immunogenic ligament or tendon xenograft for implantation into humans. The invention further provides a method for preparing a ligament xenograft by removing at least a portion of a ligament from a non-human animal to provide a xenograft; washing the xenograft in saline and alcohol; subjecting the xenograft cellular disruption treatment, such as exposure to ultraviolet radiation, immersion in alcohol, ozonation, freeze/thaw cycling, and optionally chemical crosslinking. In addition to or in lieu of the above treatments, the methods include digestion of the carbohydrate moieties of the xenograft with a glycosidase, preferably in a range of about 1 mU/ml to about 1000 U/ml, followed by treatment for sialylation. The invention also provides articles of manufacture produced by one or more of the above-identified methods of the invention. The invention further provides a ligament xenograft for implantation into a human including a portion of a ligament from a non-human animal, wherein the portion includes extracellular components and substantially only dead cells having substantially no surface α-galactosyl moieties and having sialic acid linked to at least a portion of surface carbohydrate moieties. Each of the xenografts of the invention is substantially non-immunogenic and has substantially the same mechanical properties as the respective native ligament.

37 Claims, 1 Drawing Sheet

U.S. PATENT DOCUMENTS

| | | |
|---|---|---|
| 4,678,470 | 7/1987 | Nashef et al. . |
| 4,755,593 | 7/1988 | Lauren . |
| 4,776,853 | 10/1988 | Klement et al. . |
| 4,789,663 | 12/1988 | Wallace et al. . |
| 4,801,299 | 1/1989 | Brendel et al. . |
| 4,846,835 | 7/1989 | Grande . |
| 4,880,429 | 11/1989 | Stone . |
| 4,932,973 | 6/1990 | Gendler . |
| 5,007,934 | 4/1991 | Stone . |
| 5,067,962 | 11/1991 | Campbell et al. . |
| 5,071,741 | 12/1991 | Brockbank . |
| 5,078,744 | 1/1992 | Chvapil . |
| 5,092,894 | 3/1992 | Kenny . |
| 5,116,374 | 5/1992 | Stone . |
| 5,131,850 | 7/1992 | Brockbank . |
| 5,158,574 | 10/1992 | Stone . |
| 5,160,313 | 11/1992 | Carpenter et al. . |
| 5,171,273 | 12/1992 | Silver et al. . |
| 5,171,322 | 12/1992 | Kenny . |
| 5,171,660 | 12/1992 | Carpenter et al. . |
| 5,192,312 | 3/1993 | Orton . |
| 5,216,126 | 6/1993 | Cox et al. . |
| 5,306,304 | 4/1994 | Gendler . |
| 5,306,311 | 4/1994 | Stone et al. . |
| 5,358,525 | 10/1994 | Fox et al. . |
| 5,507,810 | 4/1996 | Prewett et al. . |
| 5,613,982 | 3/1997 | Goldstein . |
| 5,944,755 * | 8/1999 | Stone ...................................... 623/16 |

OTHER PUBLICATIONS

Engkvist, Ove, *Scand. J. Plast. Reconstr. Surg.*, 13:361–369 (1982).

Collins et al., Xenotransplantation, Characterization of Porcine Endothelial Cell Determinants Recognized by Human Natural Antibodies, 1:36–46 (1994).

Satake et al., Xenotransplanation, Limited Specificity of Xenoantibodies In Diabetic Patients Transplanted With Fetal Porcine Islet Cell Clusters. Main Antibody Reactivity Against α–linked Galactose–Containing Epitopes, 1:89–101 (1994).

LaVecchio et al., Transplanatation, Enzymatic Removal of Alpha–Galactosyl Epitopes From Porcine Endothelial Cells Diminishes The CytotoxicEffect of Natural Antibodies, 60–841–847.

Stone et al., Arthroscopy: The Journal of Arthroscopic and Related Surgery, 9:234–237 (1993).

Cotterell et al., Transplantation, The Humoral Immune Response in Humans Following Cross–Perfusion of Porcine Organs, 60–861–868 (1995).

Galili, Immunology Today, 14:480–482 (1993).

Elves et al., An Investigation Into The Immunogenicity Of Various Components of Osteoarticular Grafts, *The British Journal of Experimental Pathology*, 55:344–351 (1974).

* cited by examiner

ANTERIOR CRUCIATE LIGAMENT XENOGRAFTS

RELATED APPLICATION

This application is a continuation-in-part of the copending U.S. Ser. No. 08/529,199, filed Dec. 1, 1997, which is a Continued Prosecution Application (CPA) of U.S. Ser. No. 08/529,199, filed Sep. 15, 1995.

FIELD OF THE INVENTION

The present invention relates to the field of surgical repair of injuries of the anterior cruciate ligament in the human knee using a substantially immunologically compatible ligament or tendon from a non-human animal to replace the damaged human anterior cruciate ligament.

BACKGROUND OF THE INVENTION

The anterior cruciate ligament of the knee (hereinafter the ACL) functions to resist anterior displacement of the tibia from the femur at all flexion positions. The ACL also resists hyperextension and contributes to rotational stability of the fully extended knee during internal and external tibial rotation. The ACL may play a role in proprioception. The ACL is made up of connective tissue structures composed of cells, water, collagen, proteoglycans, fibronectin, elastin, and other glycoproteins. Cyril Frank , M.D. et al., *Normal Ligament: Structure, Function, and Composition. Injury and Repair of the Musculoskeletal Soft Tissues*, 2:45–101. Structurally, the ACL attaches to a depression in the front of the intercondyloid eminence of the tibia extending posterosuperiorly to the medial wall of the lateral femoral condyle.

Partial or complete tears of the ACL are very common, comprising about 30,000 outpatient procedures in the U.S. each year. The preferred treatment of the torn ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons are used for the reconstruction; placement of intraarticular hardware is required for ligament fixation; and anterior knee pain frequently occurs. Moreover, recent reviews of cruciate ligament reconstruction indicate an increased risk of degenerative arthritis with intraarticular ACL reconstruction in large groups of patients.

A second method of treating ACL injuries, referred to as "primary repair", involves suturing the torn structure back into place. Primary ACL repair has the potential advantages of a limited arthroscopic approach, minimal disruption of normal anatomy, and an out-patient procedure under a local anesthetic. The potential disadvantage of primary cruciate ligament repair is the perception that over the long term ACL repairs do not provide stability in a sufficient number of patients, and that subsequent reconstruction may be required at a later date. The success rate of anterior cruciate ligament repair has generally hovered in the 60% to 70% range.

Much of the structure and many of the properties of original tissues may be retained in transplants through use of xenograft or heterograft materials, that is, tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel xenografts are disclosed in WO 84/03036. However, none of these disclosures describe the use of a xenograft for ACL replacement.

Once implanted in an individual, a xenograft provokes immunogenic reactions such as chronic and hyperacute rejection of the xenograft. The term "chronic rejection", as used herein, refers to an immunological reaction in an individual against a xenograft being implanted into the individual. Typically, chronic rejection is mediated by the interaction of IgG natural antibodies in the serum of the individual receiving the xenograft and carbohydrate moieties expressed on cells, and/or extracellular components. For example, transplantation of ligament or tendon xenografts from nonprimate mammals (e.g., porcine or bovine origin) into humans is primarily prevented by the interaction between the IgG natural anti-Gal antibody present in the serum of humans with the carbohydrate structure Galα1-3Galβ1-4G1cNAc-R (α-galactosyl or α-gal epitope) expressed in the xenograft. K. R. Stone et al., Porcine and bovine cartilage transplants in cynomolgus monkey: I. A model for chronic xenograft rejection, 63 Transplantation 640–645 (1997); U. Galili et al., Porcine and bovine cartilage transplants in cynomolgus monkey: II. Changes in anti-Gal response during chronic rejection, 63 Transplantation 646–651 (1997). In chronic rejection, the immune system typically responds within one to two weeks of implantation of the xenograft.

In contrast with "chronic rejection", "hyper acute rejection" as used herein, refers to the immunological reaction in an individual against a xenograft being implanted into the individual, where the rejection is typically mediated by the interaction of IgM natural antibodies in the serum of the individual receiving the xenograft and carbohydrate moieties expressed on cells. This interaction activates the complement system causing lysis of the vascular bed and stoppage of blood flow in the receiving individual within minutes to two to three hours.

The term "extracellular components", as used herein, refers to extracellular water, collagen, proteoglycans, fibronectin, elastin, and other glycoproteins present in the ligament or tendon.

Xenograft materials may be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the side chain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic ligament or tendon xenograft for implantation into a human in need of ACL repair or replacement. The invention further provides methods for processing xenogeneic ligaments or tendons with reduced immunogenicity but with substantially native elasticity and load-bearing capabilities for xenografting into humans.

As described herein, the term "ligament" also includes tendons.

As described herein, the term "xenograft" is synonymous with the term "heterograft" and refers to a graft transferred from an animal of one species to one of another species. Stedman's Medical Dictionary, Williams & Wilkins, Baltimore, Md. (1995).

As described herein, the term "xenogeneic", as in xenogeneic graft ligament, etc., refers to a graft, ligament, etc., transferred from an animal of one species to one of another species. Id.

The methods of the invention, include, alone or in combination, treatment with radiation, one or more cycles of freezing and thawing, treatment with a chemical cross-linking agent, treatment with alcohol or ozonation. In addition to or in lieu of these methods, the methods of the invention include a cellular disruption treatment and digestion of the carbodydrate moieties of the xenograft with a glycosidase in a concentration range of about 1 mU/ml to about 1000 U/ml or glycosidase digestion followed by capping of carbohydrate moieties of the xenograft with sialic acid. After one or more of the above-described processing steps, the methods of the invention provide a xenograft having substantially the same mechanical properties as a corresponding portion of a native ligament.

As described herein, the term "cellular disruption" as in, for example, cellular disruption treatment, refers to a treatment for killing cells.

As described herein, the term "capping molecules", refers to molecules which link with carbohydrate chains such that the xenograft is no longer recognized as foreign by the subject's immune system.

In one embodiment, the invention provides an article of manufacture comprising a substantially non-immunogenic ligament xenograft for implantation into a human.

In another embodiment, the invention provides a method of preparing a ligament xenograft for implantation into a human, which includes removing at least a portion of a ligament from a non-human animal to provide a xenograft; washing the xenograft in water and alcohol; and subjecting the xenograft to at least one treatment selected from the group consisting of exposure to ultraviolet radiation, immersion in alcohol, ozonation, and freeze/thaw cycling, whereby the xenograft has substantially the same mechanical properties as a corresponding portion of a native ligament As described herein, the term "portion", as in, for example, a portion of ligament or a portion of surface carbohydrate moieties, refers to all or less than all of the respective ligament or surface carbohydrate moieties.

In still another embodiment, the invention provides a method of preparing a ligament xenograft for implantation into a human, which includes removing at least a portion of a ligament from a non-human animal to provide a xenograft; washing the xenograft in water and alcohol; subjecting the xenograft to a cellular disruption treatment; digesting the xenograft with a glycosidase in a concentration range of about 1 mU/ml to about 1000 U/ml to remove substantially first surface carbohydrate moieties from the xenograft, whereby the xenograft is substantially non-immunogenic and has substantially the same mechanical properties as a corresponding portion of a native ligament.

In a further embodiment, the invention provides a method of preparing a ligament xenograft for implantation into a human, which includes removing at least a portion of a ligament from a non-human animal to provide a xenograft; washing the xenograft in water and alcohol; subjecting the xenograft to a cellular disruption treatment; digesting the xenograft with a glycosidase to remove substantially first surface carbohydrate moieties from the xenograft; and treating second surface carbohydrate moieties on the xenograft with sialic acid to cap at least a portion of the second surface carbohydrate moieties, whereby the xenograft is substantially non-immunogenic and has substantially the same mechanical properties as a corresponding portion of a native ligament.

As described herein, the terms "to cap" or "capping", refer to linking a carboydrate unit to the end of a carbohydrate chain, as in, for example, covalently linking salic acid to surface carbohydrate moieties on the xenograft.

In still further embodiments, the invention provides articles of manufacture including substantially non-immunogenic ligament xenografts for implantation into humans produced by one or more of the above-identified methods of the invention.

In yet another embodiment, the invention provides a ligament xenograft for implantation into a human which includes a portion of a ligament from a non-human animal, wherein the portion includes a extracellular components and substantially only dead cells, the extracellular matrix and the dead cells having substantially no surface $\alpha$-galactosyl moieties and having sialic acid molecules linked to at least a portion of surface carbohydrate moieties. The ligament portion is substantially non-immunogenic and has substantially the same mechanical properties as as a corresponding portion of a native ligament.

DETAILED DESCRIPTION OF THE PREFERRED EMBODIMENTS

Figure 1:
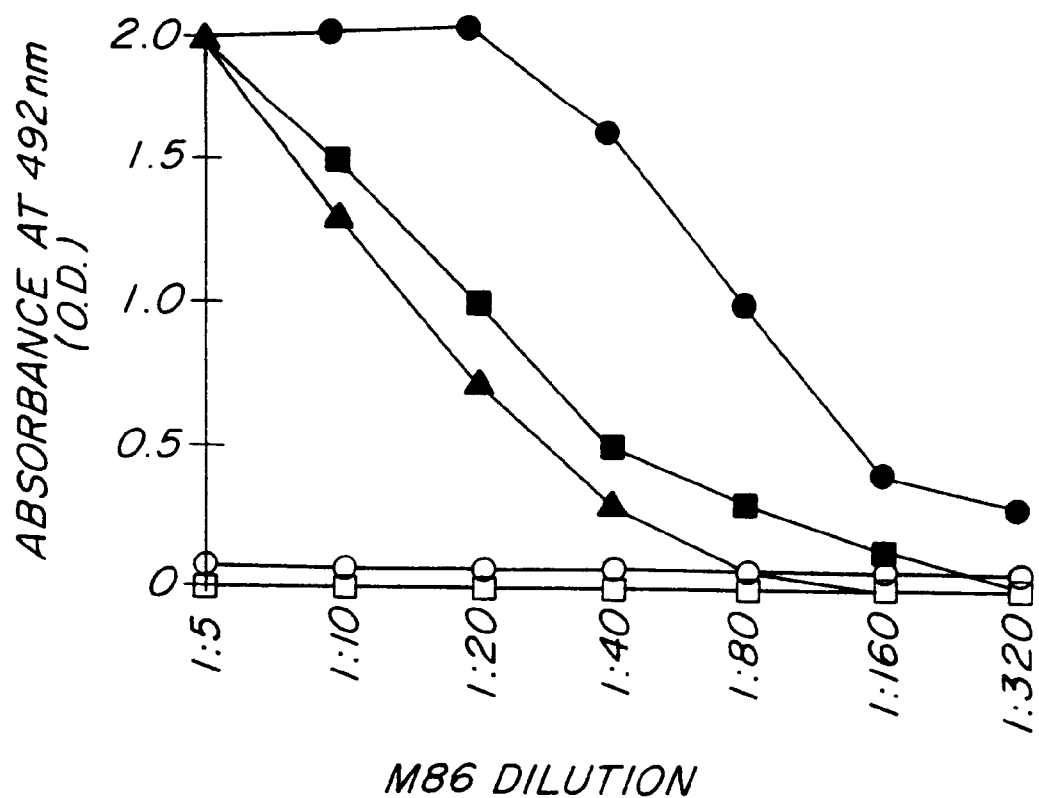
FIG. 1 is a graphical representation of the specificity of monoclonal anti-Gal antibodies for $\alpha$-galactosyl epitopes on bovine serum albumin (BSA), bovine thyroglobulin, mouse laminin, Gal$\beta$1-4 G1cNAc-BSA (N-acetyllactosamine-BSA), Gal$\alpha$1-4Gal$\beta$1-4G1cNAc-BSA (P1 antigen linked to BSA), and human thyroglobulin or human laminin.

The present invention is directed against the chronic rejection of xenografts for implantation into humans. Accordingly, the ligament xenograft produced in accordance with the method of the invention is substantially non-immunogenic, while generally maintaining the mechanical properties of a native ligament. While the ligament may undergo some shrinkage during processing, a ligament xenograft prepared in accordance with the invention will have the general appearance of a native ligament. The ligament xenograft may also be cut into segments, each of which may be implanted into the knee of a recipient as set forth below.

The invention provides, in one embodiment, a method for preparing or processing a xenogeneic ligament for engraftment into humans. The ligament may be harvested from any non-human animal to prepare the xenograft of the invention.

Ligaments from transgenic non-human animals or from genetically altered non-human animals may also be used as xenografts in accordance with the present invention. Preferably, bovine joints serve as sources of the ligament used to prepare the xenografts. More preferably, immature joints from immature animals are the sources of the ligament, since the tissue of younger animals may be inherently more elastic and engraftable than that of older animals. Most preferably, the age of the source animal is between six and eighteen months at time of slaughter. Additionally, the patellar tendon, the anterior or posterior cruciate ligaments, the Achilles tendon, or the hamstring tendons may be harvested from the animal source and used as a donor ligament.

In the first step of the method of the invention, an intact ligament is removed from the knee of a non-human animal. The joint which serves as the source of the ligament should be collected from freshly killed animals and preferably immediately placed in a suitable sterile isotonic or other tissue preserving solution. Harvesting of the joints should occur as soon as possible after slaughter of the animal and preferably should be performed in the cold, i.e., in the approximate range of about 5° C. to about 20° C., to minimize enzymatic degradation of the ligament tissue.

The ligaments are harvested from the joints in the cold, under strict sterile technique. The joint is opened by standard surgical technique. Preferably, the ligament is harvested with a block of bone attached to one or both ends, although in some forms of the invention the ligament alone is harvested. In one form of the invention, a block of bone representing a substantially cylindrical plug of approximately 9–10 mm in diameter by 20–40 mm in length may be left attached to the ligament. The ligament is carefully identified and dissected free of adhering tissue, thereby forming the xenograft.

The xenograft is then washed in about ten volumes of sterile cold water to remove residual blood proteins and water soluble materials. The xenograft is then immersed in alcohol at room temperature for about five minutes, to sterilize the tissue and to remove non-collagenous materials.

After alcohol immersion, the xenograft may be directly implanted into a knee. Alternatively, the xenograft may be subjected to at least one of the following treatments: radiation treatment, treatment with alcohol or ozonation, one or more cycles of freezing and thawing, and treatment with a chemical cross-linking agent. When more than one of these treatments is applied to the xenograft, the treatments may occur in any order.

In one embodiment of the method of the invention, the xenograft may be treated by exposure to ultraviolet radiation for about fifteen minutes or gamma radiation in an amount of about 0.5 to 3 MegaRad.

In another embodiment, the xenograft may be treated by again being placed in an alcohol solution. Any alcohol solution may be used to perform this treatment. Preferably, the xenograft is placed in a 70% solution of isopropanol at room temperature.

In still another embodiment, the xenograft may be subjected to ozonation.

In a further embodiment of the method of the invention, the xenograft may be treated by freeze/thaw cycling. For example, the xenograft may be frozen using any method of freezing, so long as the xenograft is completely frozen, i.e., no interior warm spots remain which contain unfrozen tissue. Preferably, the xenograft is dipped into liquid nitrogen for about five minutes to perform this step of the method. More preferably, the xenograft is frozen slowly by placing it in a freezer. In the next step of the freeze/thaw cycling treatment, the xenograft is thawed by immersion in an isotonic saline bath at room temperature (about 25° C.) for about ten minutes. No external heat or radiation source is used, in order to minimize fiber degradation.

In yet a further embodiment, the xenograft may optionally be exposed to a chemical agent to tan or crosslink the proteins within the extracellular proteins, to further diminish or reduce the immunogenic determinants present in the xenograft. Any tanning or crosslinking agent may be used for this treatment, and more than one crosslinking step may be performed or more than one crosslinking agent may be used in order to ensure complete crosslinking and thus optimally reduce the immunogenicity of the xenograft. For example, aldehydes such as glutaraldehyde, formaldehyde, adipic dialdehyde, and the like, may be used to crosslink the extracellular collagen in accordance with the method of the invention. Other suitable crosslinking agents include aliphatic and aromatic diamines, carbodiimides, diisocyanates, and the like. When glutaraldehyde is used as the crosslinking agent, for example, the xenograft may be placed in a buffered solution containing about 0.05 to about 5.0% glutaraldehyde and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from three to five days. Alternatively, the xenograft can be exposed to a crosslinking agent in a vapor form, including, but not limited to, a vaporized aldehyde crosslinking agent, such as, for example, vaporized formaldehyde. The vaporized crosslinking agent can have a concentration and a pH and the xenograft can be exposed to the vaporized crosslinking agent for a period of time suitable to permit the crosslinking reaction to occur. For example, the xenograft can be exposed to vaporized crosslinking agent having a concentration of about 0.05 to about 5.0% and a pH of about 7.4, for a period of time which can be from one to fourteen days, and preferably from three to five days. Exposure to vaporized crosslinking agent can result in reduced residual chemicals in the xenograft from the crosslinking agent exposure. The crosslinking reaction should continue until the immunogenic determinants are substantially removed from the xenogeneic tissue, but the reaction should be terminated prior to significant alterations of the mechanical properties of the xenograft. When diamines are also used as crosslinking agents, the glutaraldehyde crosslinking should occur after the diamine crosslinking, so that any unreacted diamines are capped. After the crosslinking reactions have proceeded to completion as described above, the xenograft should be rinsed to remove residual chemicals, and 0.01–0.05 M glycine may be added to cap any unreacted aldehyde groups which remain.

In addition to or in lieu of the above treatments, the xenograft can be subjected to a cellular disruption treatment to kill the xenograft's cells, which precedes or follows digestion of the xenograft with glycosidases to remove surface carbohydrate moieties from the xenograft. The glycosidase concentration is in a range about 1 mU/ml to about 1000 U/ml, and preferably, in the range of about 10 U/ml to about 500 U/ml, and most preferably, in the range of about 100 U/ml to 200 U/ml. The glycosidase digestion in turn can be followed by linkage with capping molecules such as sialic acid to cap surface N-acetyllactosamine ends of carbohydrate chains of the xenograft.

In an embodiment of this method of the invention, the xenograft is subjected to a cellular disruption treatment to kill the cells of the ligament prior to in vitro digestion of the xenograft with glycosidases. Typically after surface carbohydrate moieties have been removed from nucleated cells and extracellular components, nucleated cells, i.e., living cells reexpress the surface carbohydrate moieties. Reexpression of antigenic moieties of a xenograft can provoke continued immunogenic rejection of the xenograft. In contrast, non-nucleated, i.e., dead cells, are unable to reexpress surface carbohydrate moieties. Removal of antigenic surface carbohydrate moieties from the non-nucleated cells and extracellular components of a xenograft substantially permanently eliminates antigenic surface carbohydrate moieties as a source of immunogenic rejection of the xenograft.

Accordingly, in the above-identified embodiment, the xenograft of the present invention is subjected to freeze/thaw cycling as discussed above to disrupt, i.e., to kill the cells of the ligament. Alternatively, the xenograft of the present invention is treated with gamma radiation having an amount of 0.2 MegaRad up to about 3 MegaRad. Such radiation kills the ligament cells and sterilizes the xenograft. Once killed, the ligament cells are no longer able to reexpress antigenic surface carbohydrate moieties such α-gal epitopes which are factors in the immunogenic rejection of the transplanted xenografts.

Either before or after the ligament cells are killed, the xenograft is subjected to in vitro digestion of the xenograft with glycosidases, and specifically galactosidases, such as α-galactosidase, to enzymatically eliminate antigenic surface carbohydrate moieties. In particular, α-gal epitopes are eliminated by enzymatic treatment with α-galactosidases, as shown in the following reaction:

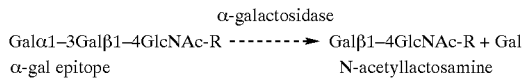

The N-acetyllactosamine residues are epitopes that are normally expressed on human and mammalian cells and thus are not immunogenic. The in vitro digestion of the xenograft with glycosidases is accomplished by various methods. For example, the xenograft can be soaked or incubated in a buffer solution containing glycosidase. In addition, the xenograft can be pierced to increase permeability, as further described below. Alternatively, a buffer solution containing the glycosidase can be forced under pressure into the xenograft via a pulsatile lavage process.

Elimination of the α-gal epitopes from the xenograft diminishes the immune response against the xenograft. The α-gal epitope is expressed in nonprimate mammal and in New World monkeys (monkeys of South America) as $1 \times 10^6 - 35 \times 10^6$ epitopes per cell, as well as on macromolecules such as proteoglycans of the extracellular components. U. Galili et al., Man, apes, and Old World monkeys differ from other mammals in the expression of α-galactosyl epitopes on nucleated cells, 263 J. Biol. Chem. 17755 (1988). This epitope is absent in Old World primates (monkeys of Asia and Africa and apes) and humans, however. Id. Anti-Gal is produced in humans and primates as a result of an immune response to α-gal epitope carbohydrate structures on gastrointestinal bacteria. U. Galili et al., Interaction between human natural anti-α-galactosyl immunoglobulin G and bacteria of the human flora, 56 Infect. Immun. 1730 (1988); R. M. Hamadeh et al., Human natural anti-Gal IgG regulates alternative complement pathway activation on bacterial surfaces, 89 J. Clin. Invest. 1223 (1992). Since nonprimate mammals produce α-gal epitopes, xenotransplantation of xenografts from these mammals into primates results in rejection because of primate anti-Gal binding to these epitopes on the xenograft. The binding results in the destruction of the xenograft by complement fixation and by antibody dependent cell cytotoxicity. U. Galili et al., Interaction of the natural anti-Gal antibody with α-galactosyl epitopes: A major obstacle for xenotransplantation in humans, 14 Immunology Today 480 (1993); M. Sandrin et al., Anti-pig IgM antibodies in human serum react predominantly with Galα1-3Gal epitopes, 90 Proc. Natl. Acad. Sci. USA 11391 (1993); H. Good et al., Identification of carbohydrate structures which bind human anti-porcine antibodies: implications for discordant grafting in man. 24 Transplant. Proc. 559 (1992); B. H. Collins et al., Cardiac xenografts between primate species provide evidence for the importance of the α-galactosyl determinant in hyperacute rejection, 154 J. Immunol. 5500 (1995). Furthermore, xenotransplantation results in major activation of the immune system to produce increased amounts of high affinity anti-Gal. Accordingly, the substantial elimination of α-gal epitopes from cells and from extracellular components of the xenograft, and the prevention of reexpression of α-gal epitopes can diminish the immune response against the xenograft associated with anti-Gal antibody binding with α-gal epitopes.

Following treatment with glycosidase, the remaining carbohydrate chains (e.g., glycosaminoglycans) of the xenograft are optionally treated with capping molecules to cap at least a portion of the remaining carbohydrate chains. This capping treatment involves capping molecules having a concentration range of about 0.01 mM to about 100 mM, and preferably, a concentration of about 0.1 mM to about 10 mM, and most preferably, a concentration of about 1 mM to about 4 mM. Treatment with capping molecules is applicable to both glycosidase-treated and non-glycosidase-treated xenografts. For example, xenografts from knock out animals which may lack α-gal epitopes may be treated with capping molecules to cap carbohydrate moieties on the xenograft, thereby reducing the xenograft's immunogenicity. Examples of capping molecules used in the present invention include fucosyl, n-acetyl glucosamine and sialic acid.

In addition, selected capping molecules, such as sialic acid, are negatively charged. The replacement of α-gal epitopes with negatively charged molecules can further diminish immunogenic rejection of the xenograft. It is theorized that the decreased immunogenicity of the xenograft results because the negative charges conferred by the capping molecules repel negatively charged antibody molecules and/or cells of the immune system, thereby masking immunogenic regions of the xenograft.

In general, electrostatic repulsion termed "zeta potential," prevents the interaction between molecules, other than ligands and their corresponding receptors, in the body, and serves as a barrier against nonspecific interactions. For example, sialic acid on carbohydrate chains of envelope glycoproteins helps infectious viruses to evade effective recognition by antibodies and by antigen presenting cells. T. W. Rademacher et al., Glycobiology, Ann. Rev. Biochem., 57:785 (1988). Bacteria such as *Neisseria gonorrhea* can prevent their immune destruction by coating themselves with sialic acid using a bacterial sialyltransferase. R. F. Rest et al., *Neisseria sialyltransferases* and their role in pathogenesis, Microbial Pathogenesis, 19:379 (1995). Similarly, the protozoan *Trypanosoma cruzi* can infect humans and cause Chagas' disease because of effective sialylation of its cell surface glycoproteins with sialic acid by use of the enzyme transialidase which transfers sialic acid from host glycoproteins to carbohydrate chains on the parasite's membrane. O. Previato et al., Incorporation of sialic acid into *Trypanosoma cruzi* macromolecules, A proposal for new metabolic route, Mol. Biochem. Parasitol., 16:85 (1985); B. Zingales et al., Direct sialic acid transfer-from a protein donor to glycolipids of trypomastigote forms of *Trypanosoma cruzi*, Mol. Biochem. Parasitol., 26:1335 (1987). Decreasing immunogenicity by sialic acid is a method also used by mammalian cells. Normal antigen presenting cells prevent nonspecific adhesion with T lymphocytes by the expression of a highly sialylated protein named sialophorin (also termed CD43). E. Famole-Belasio et al., Antibodies against sialophorin (CD43) enhance the capacity of dendritic cells to cluster and activate T lymphocytes., J. Immunol., 159:2203 (1997). Many malignant cell types that acquire metastatic properties, increase the expression of sialic acid on their cell surface glycoproteins and thus mask their tumor antigens and decrease the possibility of their detection and destruction by the immune system. G. Yogeswarren et al., Metastatic potential is positively correlated with cell surface sialylation of cultural murine cells, Science, 212:1514 (1981); J. W. Dennis, Changes in glycosylation associated with malignant transformation and tumor progression. In: Cell surface carbohydrates and cell development, M. Fukuda, Ed. CRC Press, pp. 161–213 (1992).

The same strategy for prevention of immune recognition can be implemented by treatment of α-galactosidase treated xenografts with negatively charged molecules. The addition of negatively charged molecules to the ends of the carbohydrate chains on the cells and/or on the extracellular molecules of the α-galactosidase treated xenografts can mask the non-α-Gal antigens of the xenograft and diminish immunogenic rejection of the xenograft.

Sialic acid is a non-limiting example of a negatively charged capping molecule used to cap the carbohydrate chains of the xenograft of the present invention. Sialic acid can be linked in vitro to the carbohydrate chains of the xenograft by sialyltransferase (ST), preferably in a concentration of about 1 mU/ml to about 1000 U/ml, and more preferably in a concentration of about 10 U/ml to about 200 U/ml, in the following exemplary reaction:

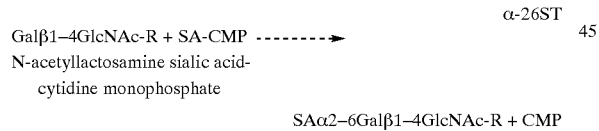

Galβ1–4GlcNAc-R + SA-CMP $\xrightarrow{\alpha\text{-26ST}}$
N-acetyllactosamine sialic acid-
   cytidine monophosphate SAα2–6Galβ1–4GlcNAc-R + CMP Sialic acid can also be linked in vitro to the carbohydrate chains of the xenograft by recombinant trans-sialidase (TS), preferably in a concentration of about 1 mU/ml to about 1000 U/ml, and more preferably in a concentration of about 10 U/ml to about 200 U/ml, in the following exemplary reaction:

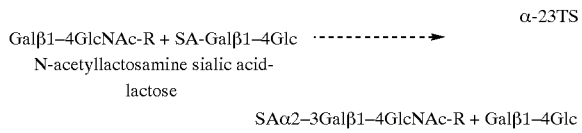

Galβ1–4GlcNAc-R + SA-Galβ1–4Glc $\xrightarrow{\alpha\text{-23TS}}$
N-acetyllactosamine sialic acid-
   lactose SAα2–3Galβ1–4GlcNAc-R + Galβ1–4Glc Prior to treatment, the outer surface of the xenograft may optionally be pierced to increase permeability to agents used to render the xenograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the xenograft. Piercing may also be performed with a laser. In one form of the invention, one or more straight lines of punctures about three millimeters apart are established circumferentially in the outer surface of the xenograft.

Prior to implantation, the ligament xenograft of the invention may be treated with limited digestion by proteolytic enzymes such as ficin or trypsin to increase tissue flexibility or coated with anticalcification agents, antithrombotic coatings, antibiotics, growth factors, or other drugs which may enhance the incorporation of the xenograft into the recipient knee joint. The ligament xenograft of the invention may be further sterilized using known methods, for example, with additional glutaraldehyde or formaldehyde treatment, ethylene oxide sterilization, propylene oxide sterilization, or the like. The xenograft may be stored frozen until required for use.

The ligament xenograft of the invention, or a segment thereof, may be implanted into a damaged human knee joint by those of skill in the art using known arthroscopic surgical techniques. Specific instruments for performing arthroscopic techniques are known to those of skill in the art, which ensure accurate and reproducible placement of ligament implants. Initially, complete diagnostic arthroscopy of the knee joint is accomplished using known methods. The irreparably damaged ligament is removed with a surgical shaver. The anatomic insertion sites for the ligament are identified and drilled to accommodate a bone plug. The size of the bone plug can be about 9–10 mm in width by about 9–10 mm in depth by 20–40 mm in length. The xenogeneic ligament is brought through the drill holes and affixed with interference screws. Routine closure is performed.

This invention is further illustrated by the following Examples which should not be construed as limiting. The contents of all references and published patents and patent applications cited throughout the application are hereby incorporated by reference.

EXAMPLE 1

Assay For α-Gal Epitopes' Elimination From Ligament By α-Galactosidase

In this example, an ELISA assay for assessing the elimination of α-gal epitopes from ligament is conducted.

A monoclonal anti-Gal antibody (designated M86) which is highly specific for α-gal epitopes on glycoproteins is produced by fusion of splenocytes from anti-Gal producing knock-out mice for α 1,3 galactosyltransferase, and a mouse hybridoma fusion partner.

The specificity of M86 for α-gal epitopes on glycoproteins is illustrated in FIG. 1. M86 binds to synthetic α-gal epitopes linked to ●-bovine serum albumin (BSA), to ▲-bovine thyroglobulin which has 11 α-gal epitopes, R. G. Spiro et al., Occurrence of α-D-galactosyl residues in the thyroglobulin from several species. Localization in the saccharide chains of complex carbohydrates, 259 J. Biol. Chem. 9858 (1984); or to ■-mouse laminin which has 50 α-gal epitopes, R. G. Arumugham et al., Structure of the asparagine-linked sugar chains of laminin. 883 Biochem. Biophys. Acta 112 (1986); but not to □-human thyroglobulin or human laminin, ○-Galβ1-4 G1cNAc-BSA (N-acetyllactosamine-BSA) and galα1-4Galβ1-4G1cNAc- BSA (P1 antigen linked to BSA), all of which completely lack α-gal epitopes. Binding is measured at different dilutions of the M86 tissue culture medium.

Once the M86 antibody is isolated, the monoclonal antibody is diluted from about 1:20 to about 1:160, and preferably diluted from about 1:50 to about 1:130. The antibody is incubated for a predetermined period of time ranging between about 5 hr to about 24 hr, at a predetermined temperature ranging from about 3° C. to about 8° C. The antibody is maintained in constant rotation with fragments of ligament about 5 $\mu$m to about 100 $\mu$m in size, and more preferably with ligament fragments ranging from about 10 $\mu$m to about 50 $\mu$m in size, at various ligament concentrations ranging from about 200 mg/ml to about 1.5 mg/ml. Subsequently, the ligament fragments are removed by centrifugation at centrifugation rate ranging from about 20,000×g to about 50,000×g. The proportion of M86 bound to the ligament is assessed by measuring the remaining M86 activity in the supernatant, in ELISA with α-gal-BSA as described in the prior art in, for example, U. Galili et al., Porcine and bovine cartilage transplants in cynomolgus monkey: II. Changes in anti-Gal response during chronic rejection, 63 Transplantation 645–651 (1997). The extent of binding of M86 to the ligament is defined as a percentage inhibition of subsequent binding to α-gal-BSA. There is a direct relationship between the amount of α-gal epitopes in the ligament and the proportion of M86 complexed with the ligament fragments, thus removed from the supernatant (i.e., percentage inhibition). Subsequently, the ligament fragments are removed by centrifugation at 35,000×g and the remaining M86 in the supernatant is assessed in ELISA with α-gal-BSA as solid phase antigen.

EXAMPLE 2

Assessment Of Primate Response To Implanted Bovine Ligament Treated With α-Galactosidase In this example, bovine ligament implants are treated with α-galactosidase to eliminate α-galactosyl epitopes, the implants are transplanted into cynomolgus monkeys, and the primate response to the ligament implants is assessed.

A bovine stifle joint is sterilely prepared and a ligament with a block of bone attached to one or both ends is removed in the cold, under strict sterile technique. A block of bone representing a substantially cylindrical plug of approximately 9 mm in diameter by 40 mm in length is left attached to the ligament. The ligament is carefully identified and dissected free of adhering tissue, thereby forming the xenograft.

The xenograft is then washed for at least five minutes with an alcohol, such as ethanol or isopropanol, to remove synovial fluid and lipid soluble contaminants.

The ligament specimen is frozen at a temperature of about −70° C. to disrupt, that, is to kill, the ligament specimen's cells.

Each ligament specimen is cut into two portions. The first portion is immersed in a buffer, such as citrate buffer solution, with a pH ranging from about 5 to about 6. The buffer contains α-galactosidase at a concentration ranging from about 50 U/ml to about 300 U/ml and an additive, such as PEG, ranging in a concentration of about 2% to about 6%. The ligament/α-galactosidase buffer solution is incubated at a temperature ranging from about 25° C. to about 32° C. for a predetermined period of time ranging from about one hr to about six hr.

At the end of the incubation, the first portion is washed under conditions which allow the enzyme to diffuse out. For example, in the present example, the ligament is washed twice with citrate buffer and three times with phosphate-buffered saline (PBS) pH 7.5. Each wash can include incubation in 50 ml of buffer solution for 10 min with gentle rocking at 24° C. Other washing procedures known to those of ordinary skill in the art can also be used. Assays are performed to confirm the complete removal of the α-gal epitopes.

Confirmation of complete removal of α-gal epitopes is performed using the ELISA inhibition assay with the monoclonal anti-Gal M86 antibody, as described above in Example 1. The α-galactosidase is produced according to the methods known in the prior art, such as, for example, the methods described in A. Zhu et al., Characterization of recombinant α-galactosidase for use in seroconversion from blood group B to O of human erythrocytes, 827 Arch. Biochem. Biophysics 324 (1996); A. Zhu et al., High-level expression and purification of coffee bean α-galactosidase produced in the yeast Pichia pastoris, 827 Arch. Biochem. Biophysics 324 (1996).

Each ligament sample is implanted in the supra patellar pouch of six cynomolgus monkeys. With the animals under general inhalation anesthesia, the anatomic insertion sites for the xenogeneic ligament are identified and drilled to accommodate a substantially 9 mm in diameter by 40 mm in length bone plug. The xenogeneic ligament is brought through the drill holes and affixed with interference screws. The procedure is performed under sterile surgical technique, and the wounds are closed with 3-0 vicryl or a suitable equivalent known to those of ordinary skill in the art. The animals are permitted unrestricted cage activity and monitored for any sign of discomfort, swelling, infection, or rejection. Blood samples (e.g., 2 ml) are drawn periodically (e.g., every two weeks) for monitoring of antibodies.

The occurrence of an immune response against the xenograft is assessed by determining anti-Gal and non-anti-Gal anti-cartilage antibodies (i.e., antibodies binding to cartilage antigens other than the α-gal epitopes) in serum samples from the transplanted monkeys. At least two ml blood samples are drawn from the transplanted monkeys on the day of implant surgery and at periodic (e.g., two week) intervals post-transplantation. The blood samples are centrifuged and the serum samples are frozen and evaluated for the anti-Gal and other non-anti-Gal anti-cartilage antibody activity.

Anti-Gal activity is determined in the serum samples in ELISA with α-gal-BSA as solid phase antigen, according to methods known in the prior art, such as, for example, the methods described in Galili et al., Porcine and bovine cartilage transplants in cynomolgus monkey: II. Changes in anti-Gal response during chronic rejection, 63 Transplantation 645–651 (1997). For example, the α-gal-BSA antigen is used to coat ELISA microtiter wells. Subsequent to blocking of the wells with 1% BSA in PBS, sera is added to the wells in two fold serial dilutions, and incubated for 2 hr at room temperature. The plates are washed, and incubated with secondary anti-IgG antibody conjugated to peroxidase. Color reaction is performed with o-phenylenediamine. Anti-Gal activity at the various post-transplantation serum dilutions are compared with the baseline pretransplantation serum.

Assays are conducted to determine whether α-galactosidase treated xenografts induce the formation of anti-ligament antibodies. For measuring anti-ligament antibody activity, an ELISA assay is performed according to methods known in the prior art, such as, for example, the methods described in K. R. Stone et al., Porcine and bovine cartilage transplants in cynomolgus monkey: I. A model for chronic xenograft rejection, 63 Transplantation 640–645 (1997). For example, a solution of ligament homogenate at 100 µg/ml in carbonate buffer is used as solid phase antigen. Other buffers known to those of ordinary skill in the art can also be used. Approximately 5 µg of ligament antigens per well are dried and the wells are blocked with BSA. The serum samples used for this assay are depleted of anti-Gal by adsorption on rabbit red cells for 30 min at 4° C. (at 3:1 ration vol/vol). Under these conditions, all anti-Gal antibodies are adsorbed on the many α-gal epitopes expressed on rabbit red cells. U. Galili et al., Evolutionary relationship between the anti-Gal antibody and the Galα163Gal epitope in primates, 84 Proc. Natl. Acad. Sci. (USA) 1369 (1987); U. Galili et al., Contribution of anti-Gal to primate and human IgG binding to porcine endothelial cells, 60 Transplantation 210 (1995). The adsorbed sera at various dilutions are analyzed for anti-ligament antibodies by ELISA, and the post-transplantation production of such antibodies are assessed by comparing this antibody activity with that observed in the pretransplantation serum.

The ligament xenograft is optionally explanted at one to two months post-transplantation, sectioned and stained for histological evaluation of inflammatory infiltrates. Post-transplantation changes in anti-Gal and other anti-ligament antibody activities are correlated with the inflammatory histologic characteristics (i.e., granulocytes or mononuclear cell infiltrates) within the explanted ligament, one to two months post-transplantation, using methods known in the art, as, for example, the methods described in K. R. Stone et al., Porcine and bovine cartilage transplants in cynomolgus monkey: I. A model for chronic xenograft rejection, 63 Transplantation 640–645 (1997).

Where the xenogeneic ligament is explanted, the ligament xenograft is aseptically harvested. At the time of the xenograft removal, joint fluid, if present in amounts sufficient to aspirate, is collected from the stifle joints for possible immunologic testing if the gross and histopathologic evaluation of the transplants indicate good performance of the transplanted ligament.

A portion of the implant and surrounding tissue is frozen in an embedding medium for frozen tissue specimens in embedding molds for immunohistochemistry evaluation according to the methods known in the prior art. "TISSUE-TEK®" O.C.T. compound which includes 10.24% w/w polyvinyl alcohol, 4.26% w/w polyethylene glycol, and 86.60% w/w nonreactive ingredients, and is manufactured by Sakura FinTek, Torrence, Calif., is a non-limiting example of a possible embedding medium for use with the present invention. Other embedding mediums known to those of ordinary skill in the art may also be used. The remaining implant and surrounding tissue is collected in 10% neutral buffered formalin for histopathologic examination.

EXAMPLE 3

Assessment Of Primate Response To Implanted Ligament Treated With α-Galactosidase, Sialic Acid-Cytosine Monophosphate and Sialyltransferase In this example, bovine ligament implants are treated with α-galactosidase to eliminate α-gal epitopes, as described in Example 2. The implants are further treated with sialic acid-cytosine monophosphate (SA-CMP) and sialyltransferase to cap carbohydrate chains with sialic acid. Sialyltransferase facilitates the transfer of the sialic acid from the SA-CMP compound to the xenograft. The sialic acid links to and thus caps the carbohydrate chains. The cytosine monophosphate provides the necessary energetic level to the sialic acid for such linking and capping. Capping with sialic acid interferes with the ability of the the subject's immune system to recognize the xenograft as foreign. The negative charge of the sialic acid further interferes with the ability of the ligament antigens to bind with non-anti-Gal anti-cartilage antibodies (i.e., antibodies binding to ligament antigens other than the α-gal epitopes.) The implants are transplanted into cynomolgus monkeys, and the primate response to the ligament implants is assessed.

Bovine ligament stifle joints are prepared as described in Example 2 including the α-galactosidase treatment. Prior to implantation into the monkeys, however, the implants are further treated with a predetermined amount of a predetermined amount of SA-CMP and sialyltransferase, at specified concentrations for a predetermined time and at a predetermined temperature, to cap carbohydrate chains with sialic acid. For example, the sample is immersed in 10 ml buffer solution at a pH of about 5.5 to 7.0, and preferably a pH of about 6.0–6.5, and most preferably a pH of about 6.2, containing SA-CMP at a concentration of approximately about 1 mM to about 10 mM, and sialyltransferase at a concentration of about 100 U/ml. The sample is incubated at a temperature range of about 26° C. to about 37° C. for a predetermined time period of about one hr to about four hr.

Other enzymes such as recombinant transialidase can be used to facilitate the transfer of sialic acid from compounds such as sialylated lactose to the xenograft.

Further, other molecules, such as fucosyl in combination with the corresponding fucosyltransferase and n-acetyl glucosamine in combination with the corresponding glycosyltransferase, can also be used for capping the carbohydrate chains of the implants.

Subsequently, the samples are washed to remove the enzyme and implanted into the monkeys, and the occurrence of an immune response against the xenograft is assessed as described above in Example 2.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. A method of preparing a ligament xenograft for implantation into a human, which comprises,
   a. removing at least a portion of ligament from a joint of a non-human animal to provide a xenograft;
   b. washing the xenograft in water and alcohol;
   c. subjecting the xenograft to a cellular disruption treatment;
   d. digesting the xenograft with a glycosidase to remove substantially a plurality of first cell surface carbohydrate moieties from the xenograft, wherein the glycosidase has a concentration in the range of about 1 mU/ml to about 1000 U/ml, and
   e. treating a plurality of second cell surface carbohydrate moieties on the xenograft with a plurality of sialic acid molecules to cap at least a portion of the second cell surface carbohydrate moieties, wherein the sialic acid molecules have a concentration in a range of about 0.01 mM to about 100 mM, whereby the xenograft is substantially non-immunogentic and has substantially the same mechanical properties a corresponding portion of native human ligament.

2. The method of claim 1, wherein the glycosidase is a galactosidase.

3. The method of claim 2, wherein the galactosidase is an α-galactosidase.

4. The method of claim 1, wherein the cellular disruption treatment comprises freeze/thaw cycling.

5. The method of claim 1, wherein the cellular disruption treatment comprises exposure to gamma radiation.

6. The method of claim 1, wherein the removing step comprises removing with the portion a first block of bone attached to a first end of the portion.

7. The method of claim 1 wherein the removing step comprises removing with the portion a second block of bone affixed to a second end of the portion opposite the first end.

8. The method of claim 1 further comprising the step of following step c, exposing the xenograft to a crosslinking agent in a vapor form.

9. A method of preparing a ligament xenograft for implantation into a human, which comprises
   a. removing at least a portion of a ligament from a non-human animal to provide a xenograft;
   b. washing the xenograft in water and alcohol;
   c. subjecting the xenograft to a cellular disruption treatment;
   d. digesting the xenograft with a glycosidase to remove substantially a plurality of first cell surface carbohydrate moieties from the xenograft; and
   e. treating a plurality of second cell surface carbohydrate moieties on the xenograft with a plurality of sialic acid molecules to cap at least a portion of the second surface carbohydrate moieties,
      whereby the xenograft is substantially non-immunogenic and has substantially the same mechanical properties as a corresponding portion of a native human ligament.

10. The method of claim 9, wherein the capping step comprises treating the second cell surface carbohydrate moieties on the xenograft with the sialic acid molecules having a concentration in a range of about 0.01 mM to about 100 mM.

11. The method of claim 9, wherein at least the glycosidase is a galactosidase.

12. The method of claim 11, wherein at least the galactosidase is an α-galactosidase.

13. The method of claim 9, wherein the cellular disruption treatment comprises freeze/thaw cycling.

14. The method of claim 9, wherein the cellular disruption treatment comprises exposure to gamma radiation.

15. The method of claim 9, wherein the removing step comprises removing with the portion a first block of bone attached to a first end of the portion.

16. The method of claim 15, wherein the removing step comprises removing with the portion a second block of bone affixed to a second end of the portion opposite the first end.

17. The method of claim 9 further comprising the step of following step c, exposing the xenograft to a crosslinking agent in a vapor form.

18. An article of manufacture comprising a substantially non-immunogenic ligament xenograft for implantation in to a human, produced by
   a. removing at least a portion of a ligament from a non-human animal to provide a xenograft;
   b. washing the xenograft in water and alcohol;
   c. subjecting the xenograft to a cellular disruption treatment; and
   d. digesting the xenograft with a glycosidase to remove substantially a plurality of first cell surface carbohydrate moieties from the xenograft, wherein the glycosidase has a concentration in the range of about 1 mU/ml to about 1000 U/ml and
   e. treating a plurality of second cell surface carbohydrate moieties on the xenograft with a plurality of sialic acid capping molecules to cap at least a portion of the second surface carbohydrate moieties on the xenograft wherein the sialic acid capping molecules have a concentration in a range of about 0.01 mM to about 100 mM,
      whereby the xenograft is substantially non-immunogenic and has substantially the same mechanical properties as a corresponding portion of a native human ligament.

19. The article of manufacture of claim 18, wherein the glycosidase is a galactosidase.

20. The article of manufacture of claim 19, wherein the galactosidase is an α-galactosidase.

21. The article of manufacture of claim 18, wherein the cellular disruption treatment comprises freeze/thaw cycling.

22. article of manufacture of claim 18, wherein the cellular disruption treatment comprises exposure to gamma radiation.

23. article of manufacture of claim 18, wherein the removing step comprises removing with the portion a first block of bone attached to a first end of the portion.

24. The article of manufacture of claim 23, wherein the removing step comprises removing with the portion a second block of bone affixed to a second end of the portion opposite the first end.

25. article of manufacture of claim 18, further comprising the step of following step c, exposing the xenograft to a crosslinking agent in a vapor form.

26. An article of manufacture comprising a substantially non-immunogenic ligament xenograft for implantation in to a human, produced by
   a. removing at least a portion of a ligament from a non-human animal to provide a xenograft;
   b. washing the xenograft in water and alcohol;
   c. subjecting the xenograft to a cellular disruption treatment;
   d. digesting the xenograft with a glycosidase to remove substantially a plurality of first cell surface carbohydrate moieties from the xenograft; and
   e. treating a plurality of second cell surface carbohydrate moieties on the xenograft with a plurality of sialic acid molecules to cap at least a portion of the second cell surface carbohydrate moieties, whereby the xenograft is substantially non-immunogenic and has substantially the same mechanical properties as a corresponding portion of a native human ligament.

27. The article of manufacture of claim 26, wherein the sialic acid molecules have a concentration in a range of about 0.01 mM to about 100 mM.

28. The article of manufacture of claim 26, wherein the glycosidase is a galactosidase.

29. The article of manufacture of claim 28, wherein the galactosidase is an α-galactosidase.

30. The article of manufacture of claim 26, wherein the cellular disruption treatment comprises freeze/thaw cycling.

31. The article of manufacture of claim 26, wherein the cellular disruption treatment comprises exposure to gamma radiation.

32. The article of manufacture of claim 26, wherein the removing step comprises removing with the portion a first block of bone attached to a first end of the portion.

33. The article of manufacture of claim 32, wherein the removing step comprises removing with the portion a second block of bone affixed to a second end of the portion opposite the first end.

34. The article of manufacture of claim 26 further comprising the step of following step c, exposing the xenograft to a crosslinking agent in a vapor form.

35. A ligament xenograft for implantation into a human comprising a portion of a ligament from a non-human animal, wherein the portion includes a plurality of extracellular components and a plurality of substantially only dead cells, the extracellular components and the dead cells having substantially no surface α-galactosyl moieties and having a plurality of sialic acid molecules linked to at least a portion of a plurality of surface carbohydrate moieties on the xenograft, whereby the portion of the ligament is substantially non-immunogenic and has substantially the same mechanical properties as a corresponding portion of a native human ligament.

36. The ligament xenograft of claim 35, wherein the portion of the ligament has a first block of bone attached to a first end thereof.

37. The ligament xenograft of claim 36, wherein the portion of the ligament has a second block of bone affixed to a second end thereof opposite the first end.

* * * * *